(12) United States Patent
Hipp (10) Patent No.: US 7,683,099 B2
(45) Date of Patent: Mar. 23, 2010

(54) METHOD FOR CARRYING OUT HETEROGENEOUS CATALYTIC EXOTHERMIC GAS PHASE REACTIONS

(75) Inventor: Anton Josef Hipp, Wurzburg (DE)

(73) Assignee: Ammonia Casale S.A. (CH)

( * ) Notice: Subject to any disclaimer, the term of this patent is extended or adjusted under 35 U.S.C. 154(b) by 504 days.

(21) Appl. No.: 11/569,726

(22) PCT Filed: May 28, 2005

(86) PCT No.: PCT/EP2005/005775

§ 371 (c)(1),
(2), (4) Date: Sep. 4, 2007

(87) PCT Pub. No.: WO2005/115607

PCT Pub. Date: Dec. 8, 2005

(65) Prior Publication Data

US 2007/0293590 A1   Dec. 20, 2007

(30) Foreign Application Priority Data

May 28, 2004 (DE) ........................ 10 2004 028 200

(51) Int. Cl.
*C07C 27/00* (2006.01)
*C01C 1/01* (2006.01)
(52) U.S. Cl. ........................ 518/706; 518/705; 518/713; 423/359
(58) Field of Classification Search ............... 518/705, 518/706, 713; 423/359
See application file for complete search history.

(56) References Cited

U.S. PATENT DOCUMENTS 4,778,662 A    10/1988  Pinto
4,859,425 A    8/1989   Zardi
5,216,034 A    6/1993   Sie
5,252,609 A    10/1993  Pinto
5,631,302 A    5/1997   Konig et al.

FOREIGN PATENT DOCUMENTS

| DE | 37 08 781 A1 | 9/1988 |
| DE | 196 05 572 A1 | 8/1997 |
| EP | 0 272 449 A2 | 6/1988 |
| EP | 0 359 952 A2 | 3/1990 |
| EP | 0 682 002 A1 | 11/1995 |
| EP | 0 873 972 A2 | 10/1998 |
| EP | 1 339 641 B1 | 9/2003 |
| GB | 1 105 614 | 3/1968 |
| WO | WO 99/59945 | 11/1999 |

*Primary Examiner*—Jafar Parsa
(74) *Attorney, Agent, or Firm*—Akerman Senterfitt (57) ABSTRACT

The invention relates to a method for carrying out heterogeneous catalytic exothermic gas phase reactions at a high temperature and high pressure, during which the synthesis gas comprised of a mixture of make-up gas and/or of recycle gas is fed through at least two synthesis stages that are connected in-series to form a synthesis system. The product gases from the synthesis stages, with the exception of the last stage, are separated into at least two partial flows. One partial flow is cooled until the product is condensated out, and the condensate containing the product is separated from the gaseous constituents. Afterwards, the gaseous constituents are combined with the warm portion of the product gas in order to reach the inlet temperature of the next synthesis stage. In addition, the partial flow from which the product was condensated out and removed, can be heated before being remixed with the warm portion of the product gas. After heating, the temperature is less than that of the warm portion of the product gas, and the heat used for heating the partial flow from which the product was condensated out, is extracted, at least in part, from this partial flow during its cooling.

14 Claims, 8 Drawing Sheets

METHOD FOR CARRYING OUT HETEROGENEOUS CATALYTIC EXOTHERMIC GAS PHASE REACTIONS

FIELD OF APPLICATION

The present invention relates to a method for carrying out heterogeneous catalytic exothermic gas phase reactions, in adiabatic and non-adiabatic conditions, in view of greater conversion yields with reduced energy consumption. Examples of such heterogeneous catalytic exothermic gas phase reactions are the production of methanol from synthesis gas, the production of ammonia from mixtures containing hydrogen and nitrogen or the production of higher alcohols from synthesis gas.

PRIOR ART

The industrial production of these products is based on intense exothermic equilibrium reactions, which are less advantageous for the production of such products, wherein good reaction yields can only be achieved by use of selective catalysts. The production of these products is facilitated, from the viewpoint of the chemical equilibrium, by relatively low temperatures. The reaction speed depends on the activity of the catalyst, on temperature, and on the composition of the synthesis gas.

In predetermined reaction conditions, the temperature in the catalyst bed can exceed an acceptable level, therefore causing damage to the catalyst. The cooling of the catalyst bed may be carried out by external cooling of the converter, which fundamentally corresponds to an isothermal operating condition, or by intermediate cooling between successive adiabatic catalyst beds in one or more converters. The adiabatic methods provide smaller yields per cycle compared to isothermal methods, therefore requiring higher catalyst volumes and circulation ratios.

The technical background of the present invention is initially explained by means of methanol synthesis. In methanol synthesis, the following reactions are of particular importance:

$$CO + 2H_2 \; CH_3OH - 90.5 \; KJ/mol \tag{1}$$

$$CO_2 + 3H_2 \; CH_3OH + H_2O - 49.4 \; KJ/mol \tag{2}$$

$$CO_2 + H_2 \; CO + H_2O + 41.1 \; KJ/mol \tag{3}$$

At present, in the industrial production of methanol, only catalysts based on CuO/ZnO/Al2O3 are used. The synthesis is carried out at pressures from 20 to 120 bar and temperatures in the range of 200 to 350° C.

The synthesis gas, composed of a mixture of hydrogen with carbon monoxide and carbon dioxide, is obtained by steam reforming or auto-thermal reforming of methane gas. It is mixed with recycle gas, then pre-heated and compressed up to the synthesis pressure, the gas then reacting in a successive reactor. The conventional methanol reactors are composed of a pressurized vessel, which is provided with one or more synthesis catalyst beds, cooling gas units and/or heat exchangers, in order to pre-heat the synthesis gas and to control the reaction heat.

Raw methanol is condensed out from the outflowing reaction gas, and the unreacted gas is returned to the inlet of the synthesis reactor. A small amount is removed from the circuit, to limit the content of inert gases. The state of the art comprises the so called "quench-gas" reactors, in which the synthesis catalyst is controlled by introducing cold synthesis gas. Examples of such reactors are described in patent publications GE 1 105 614, EP 0 359 952, and U.S. Pat. No. 4,859,425.

These reactors and corresponding methods require high circulation ratios, in order to obtain high yields. In U.S. Pat. No. 4,778,662 a reactor is described, in which the generated heat is transferred to the incoming synthesis gas. In patent specifications U.S. Pat. No. 5,252,609 and U.S. Pat. No. 5,631,302 a method is described, in which the make-up gas undergoes a pre-synthesis, for reducing the cycle costs. In DE 196 05 572 A1 two synthesis reactors connected in series operate in a circuit, to reduce the circulation costs. The high carbon oxide yields are obtained with make up gases, whose CO2-to-CO ratios are less than 0.5. Also in WO 99/59945 a method is described in which the circulation reduction is obtained by means of 2 or 3 reactors connected in series and by optimization of the make-up gas distribution. Also in this case a make-up gas is used with CO2-to-CO ratios less than 0.5. These synthesis gases can only be produced with auto-thermal or combined reforming plants, which require costly oxygen plants.

The technical background of the invention is similar in ammonia producing plants. The EP 1 339 641 B1 describes for instance a method, where ammonia is generated under different pressures from synthesis gas according to the equation $$N_2 + 3H_2 \; 2NH_3 - 92.3 \; kJ/mol \tag{4}$$

To this end the synthesis gas is led through one or more synthesis systems connected in series, which are not circuit systems, and then introduced into a circuit system. After each of these synthesis systems a rise in pressure takes place and in each of these systems ammonia is obtained and extracted.

The synthesis reactors are usually of the type described in DE 37 08 781, which contains a catalyst and a heat exchanger. A connection in series of a plurality of these reactors is known, where it is always necessary to ensure that the reactor inlet temperature has a minimum value, approximately 300 to 400° C. for the most common catalyst materials, although the temperature at the reactor outlet should not exceed the maximum catalyst damaging temperature. Moreover each rise in temperature always causes a worsening of the reactor yield obtainable on the basis of the chemical equilibrium. It is therefore desirable to keep the reactor temperature as near as possible to the minimal temperature.

A number of methods exist for setting up these reactor temperatures. In EP 272 449 a method is described where, in a circuit system, at least 2 reactors are connected in-series and, before reaching the last reactor, control is provided by the fact that a partial flow of the circulation gas leaving the penultimate catalyst bed is led to a steam generator, which acts as a heat exchanger and/or to a bypass line bypassing this heat exchanger, where a partial flow of cold circulation gases can be led to said bypass line, prior to heating and feeding to the first catalyst bed, as a quench means.

The methods cited for ammonia production have however the disadvantage that the obtainable ammonia quantity is limited by the chemical reaction equilibrium in the last reactor. Since this limit is frequently reached already after 2 or 3 reactors, according to the state of the art, it is not possible to connect further reactors, if an increase in capacity is desired. Moreover, control of the temperature at variable operating conditions is costly and complex.

SUMMARY OF THE INVENTION

The object of the present invention is to provide an improved method for carrying out heterogeneous catalytic exothermic gas phase reactions at high temperature and pressure, which is suitable for plants for the production of methanol and ammonia as well as for similar synthesis of higher alcohols from synthesis gas, and which is also suitable for upgrading existing plants.

The invention solves this problem according to the independent claim, in that the synthesis gas comprised of a mixture of make-up gas and/or of recycle gas is led through at least two synthesis stages that are connected in-series to form a synthesis system, wherein the product gases from the synthesis stages, with the exception of the last stage, are separated into at least two partial flows, one partial flow is cooled until the product is condensated out, and the condensate containing the product is separated from the gaseous constituents, and, subsequently, the gaseous constituents are combined with the warm portion of the product gas in order to reach the inlet temperature of the next synthesis stage.

In embodiments of said method, the partial flow from which the product was condensated out and removed, is heated, before being remixed with the warm portion of the product gas, wherein, after heating, the temperature is less than that of the warm portion of the product gas, otherwise no reduction in the mixing temperature will be obtained after combining the partial flows. The heat used for heating the partial flow from which the product was condensated out, can be extracted, at least in part, from this partial flow during its cooling. This can be achieved by providing a gas-gas heat exchanger.

Depending on the local boundary conditions, it is advantageous and possible to use other heating systems, in particular in connection with the methods used for the condensation of the product and the production of the synthesis gas.

In a further embodiment of the method, from the portion of the product gas to be cooled, most of the heat is recovered by indirect heat exchange with boiler feed water and/or completely desalinated water.

In a further embodiment of the method, the synthesis gas fed to the first synthesis reactor is composed of from 16 to 40 Mol-% of make-up synthesis gas. A further feeding of synthesis gas between the individual reactors of the reactor system, which in this case has to be carried out as synthesis loop, is not provided.

In a further embodiment of the method, the last reactor of a synthesis system is cooled by indirect heat exchange with synthesis gas. For instance, in the synthesis of ammonia it is on the contrary common practice to cool the first reactor, since in this first reactor the most intensive reaction conditions are present—the inlet product concentrations are as low as possible in order to have the maximum possible range until the equilibrium yield is reached—and thus the temperature increases particularly rapidly due to the exothermic characteristic. In the present invention this is no longer required, since each of the reactors connected in series can operate with approximately the same inlet product concentrations. In this way it is possible to lower the outlet temperature of the last reactor and, therefore, it is possible to move the chemical equilibrium of the exothermal reaction to an advantageous operating point, further increasing the yield.

Further embodiments of the invention refer in particular to the synthesis of methanol. Hereby, from a synthesis gas containing hydrogen, carbon monoxide and carbon dioxide, methanol is produced by conversion on granular copper catalysts at pressures in the range of 20-120 bar and temperatures of 200 to 350° C., wherein the condensation is set in a partial flow among the individual reactors, so that between the first and the last synthesis stage, 15-50% of the total methanol production can be found in the separated methanol-containing condensate.

In this case, according to the invention, an adiabatic multiple bed reactor, a tube reactor with synthesis gas cooling or an isothermal reactor are preferred as the first synthesis reactor; in the latter case, the catalyst is crossed by tubes in which cooling water, boiling at an elevated pressure, flows.

In this way, it is economically possible to carry out the methanol synthesis from hydrogen, carbon monoxide and carbon dioxide, in at least two synthesis stages, even with $CO_2$-CO ratios up to 1:1 in make-up gas, so increasing yield and reducing costs. In this way, it is also possible to advantageously retrofit and, with additional external use of synthesis gas, to increase the production capacity in system loops without additional costs, up to 50%, by cooling the product mixture from the outlet temperature of a synthesis stage to the inlet temperature of the successive stage, at the same time removing raw methanol from the product mixture. Due to the fact that methanol and water are removed from the product mixture of the preceding stage, the composition of the synthesis gas for the next synthesis stage is set more advantageously at the equilibrium and, therefore, the CO and $CO_2$ conversion yield for each cycle is increased.

With the use of two synthesis stages, the method according to the invention is typically identified in that 1. make-up gas and recycle gas are led into the first synthesis stage;

2. the first product mixture is cooled to the inlet temperature of the cooling tubes of the second synthesis stage, therefore removing by partial condensation 15-50% of the total methanol production from the synthesis gas before the second synthesis stage;

3. the second synthesis stage or the second synthesis reactor is cooled by synthesis gas in an indirect heat exchange;

4. the second product mixture, from the second synthesis stage, is cooled and the raw methanol vapors are condensed;

5. from the methanol-containing condensate recycle synthesis gas is separated and mixed with make-up gas from an external source, said synthesis gas being preheated with the second product mixture and partially also with the first product mixture, up to the inlet temperature in the first synthesis stage;

6. the first synthesis stage or the first synthesis reactor is formed by a. an adiabatic multiple bed reactor, b. a reactor with indirect synthesis gas cooling, c. a reactor in which the catalyst is crossed by tubes where water boiling at elevated pressure flows as a coolant.

This permits an economic retrofit, an increase in production and a reduction in costs, also for known synthesis methods with a synthesis stage, by connecting downstream a second reactor which is indirectly cooled by synthesis gas. In the case of the addition of the invention to the known methods with adiabatic shaft reactors connected in series, 10-40% of the total methanol production is extracted between the first and the last synthesis stage from the product gas by partial condensation. This takes place as a result of the small temperature difference between the outlet temperature of one synthesis stage and the inlet temperature of the successive synthesis stage.

The partial condensation of raw methanol from the product gas with simultaneous setting of the inlet temperature in the successive synthesis stage is obtained according to the invention by separation of the product gas into two parts. One part is cooled in order to condense the methanol and water vapors, to separate the raw methanol from the synthesis gas, to recombine the cold synthesis gas with the warm portion of the product gas, in order to reach the inlet temperature in the successive synthesis stage. Cooling of the product gas until condensation of the raw methanol takes places with heat recovery. In methanol synthesis, the heat can be transferred to the boiler feed water and/or to the completely desalinated water.

Further embodiments of the invention refer in particular to ammonia synthesis. In ammonia synthesis, where the temperature of the product gas is more than 100° C. higher than in the synthesis of methanol, a portion of the heat to be removed for condensation can also be used for steam generation. The higher temperature difference between the condensation temperature and reactor inlet temperature influences the mixing ratio of the partial flows. Due to the very high difference in temperature, it is necessary to separate, cool and free from ammonia only a small partial flow, in order to obtain, after its renewed mixing with the principal flow, an adequate reactor inlet temperature. Hereby a notable enhancement with respect to the state of the art is obtained, but the potential for enhancement is not completely exploited.

Therefore, according to the dependent claims, the temperature difference between the condensation temperature and the reactor inlet temperature is artificially reduced by the fact that re-heating of the gas takes place after condensation of ammonia. Reducing the temperature difference causes a variation in the mixing ratio since a greater partial flow can be led to the condensation of ammonia, which increases the quantity of additional ammonia obtained. In the limit case it can be advantageous to maintain the partial flow from which no ammonia condenses as low as possible, using it only for control purposes.

In this way the inlet concentration of ammonia in the successive reactor is reduced, where the reaction yield and the reaction temperature rise consequently. By repeated use of the invention—splitting of the outlet flows with subsequent partial condensation, re-heating and combination of the partial flows—it is possible to recover a great part of the ammonia and therefore to generate a gas state, by reducing the ammonia concentration, which permits connection of a further reactor downstream.

Since for each reactor passage in the ammonia production, only a small part of the synthesis gas can be converted, usually 10 to 20% of the total gas quantity, enough synthesis gas is present also for further, successive reactors. In another embodiment of the invention it is therefore provided to arrange at least 3 ammonia reactors in series; economically advantageous is a series connection of 3, 4, 5, 6 or 7 reactors of the conventional type, although according to the invention also a higher number of reactors would be advantageous if, for economic reasons, in each of the reactors only a respective lower yield is desired, for instance when using cheaper catalysts and reduced reactor dimensions, which are advantageous for manufacture reasons.

This possibility to retrofit many further reactors, for instance in a loop system, but also in a make-up gas system, connected upstream to a loop system, as described in EP 1 339 641 B1, is an advantage of the invention.

In a further embodiment of the invention, a heat recovery steam generator is placed downstream from each ammonia reactor, which converts part of the reaction heat into usable steam, therefore reducing the coolant requirements in the condensation of ammonia. The heat recovery steam generator can be placed either upstream or downstream of the point where separation in partial flows according to the invention takes place; in the latter case an arrangement at each partial flow is possible.

In a further embodiment of the invention, the heating of the partial flow, from which ammonia was condensed, is supported by heat transmission from a successive reactor. For construction reasons, in special cases, for instance in the case of retrofitting using existing plant components, it can also be advantageous to provide this further heating downstream from the conjunction point of the partial flows, which is equivalent.

BRIEF DESCRIPTION OF THE DRAWINGS

In the following description some embodiments of the method according to the invention are explained by means of the drawings. In case of methanol production.

In case of ammonia production.

DETAILED DESCRIPTION OF A PREFERRED EMBODIMENT

Figure 1:
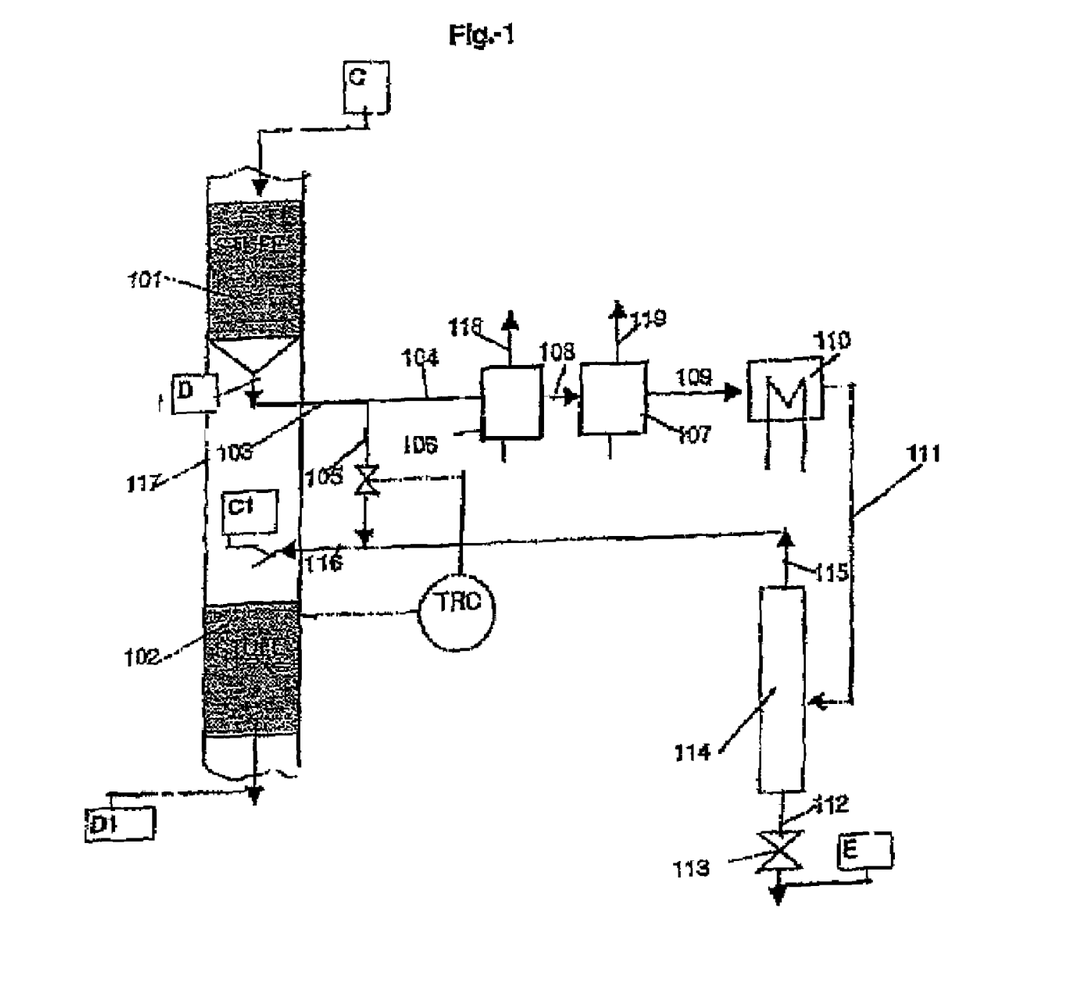
FIG. 1 shows the temperature control between the synthesis stages with product separation and heat recovery.

According to FIG. 1, a product mixture flow D flowing from a synthesis stage X1 in line 103 is divided into two portions, the first portion in line 104 is fed to the indirect heat exchanger 106, in which some of the heat contained is transferred to boiler feed water 118 and is fed through line 108 to the heat exchanger 107, where it transmits heat to the completely desalinated water 119, and is cooled down to 60° C. The preheated completely desalinated water 119 and the boiler feed water 118 are led to a steam generator plant outside the synthesis loop. The first product mixture is further fed through line 109 to the water cooler 110 and cools down to 40° C., so that the contained water and methanol vapors condense and reach the separator 114 through line 111. In the separator 114 the liquid raw methanol is separated from the gaseous components of the product gas 104 and is further fed through line 112 and the pressure-reducing valve 113 to a collecting and pressure-reducing vessel. The gaseous components flow through the separator 114 in line 115 and are combined with the second product gas component coming from line 105 and are fed through line 116 as an inlet flow C1 to the successive synthesis stage X+1 102. The inlet flow C1 at a temperature lower than flow D and freed from its water and methanol content, is therefore more advantageously controlled with respect to equilibrium and kinetics. The advantages of this method result in a much smaller circulation ratio as compared to the known adiabatic methods.

Figure 2:
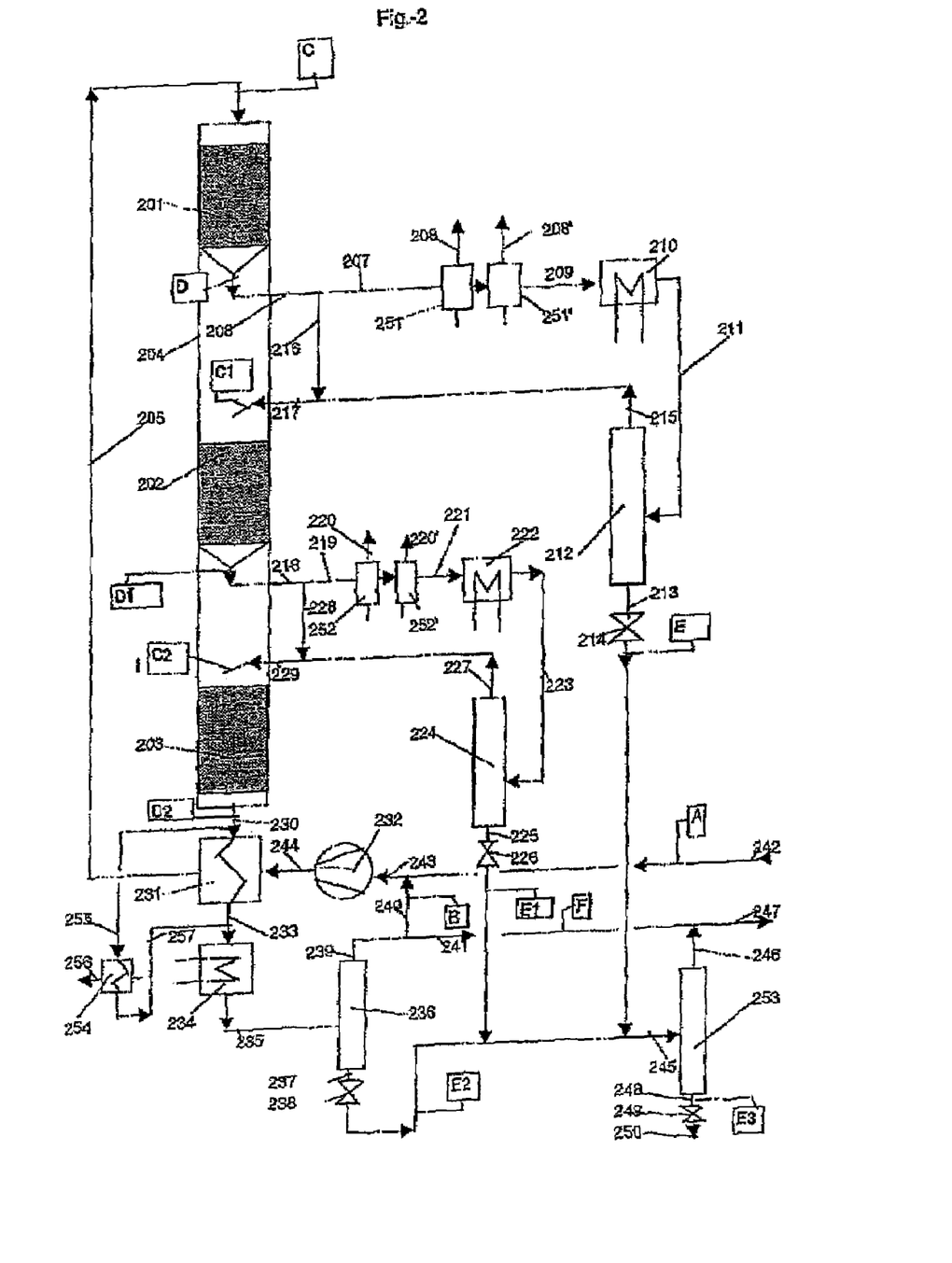
FIG. 2 shows a flow chart of the method with three adiabatic synthesis stages.

FIG. 2 shows an embodiment of the present method with three synthesis stages 201, 202 and 203, which are connected in series in a pressure resistant synthesis reactor vessel 204. The make-up gas, flow A, in line 242 mixes with the recycle gas, flow B, coming from line 240, and is drawn by the rotating compressor 232, compressed and fed through line 244 to the gas-gas heat exchanger 231. By heat exchange with the final product, gas flowing from synthesis stage 203, flow D2, line 230, is preheated to the inlet temperature in the first synthesis stage and reaches through line 205, as flow C, the first synthesis catalyst layer 201, where the reaction takes place adiabatically and the temperature rises steadily until it reaches the outlet of the catalyst.

The product mixture flow (D), from line 206 is separated into two partial flows according to the invention. The first partial flow flows through line 207 and the heat exchanger 251, where it transfers some of its heat to the boiler feed water 208. Thereafter it flows to the heat exchanger 251', where it transfers heat to the completely desalinated water 208' and cools down to 60° C. It then reaches, through line 209, the water cooler 210, cools down to 40° C., water and methanol vapors condense and are separated from the gaseous components in the separator 212. The mixture containing liquid methanol is withdrawn through line 213 and the pressure-reducing valve 214, as a first raw methanol product flow E, from the synthesis loop, and is fed to the intermediate pressure-reducing vessel 253 through the collecting line 245. The gaseous components are drawn from the separator 212 through line 215 and are then recombined with the second product gaseous portion from line 216, in line 217, forming the inlet flow C1 of synthesis stage 202.

The product gas of the second synthesis stage, flow D1, from line 218, is also separated into two flows, line 219 and line 228. The product mixture from line 219 is fed to the heat exchanger 252, whereby some of the heat is transferred to the boiler feed water 220. Thereafter, in the heat exchanger 252', heat is transmitted to the desalinated water and the product mixture is cooled down to 60° C. This mixture reaches, through line 221, the water cooler 222, cools down to 40° C., the water and methanol vapors condense and are separated from the gaseous components in the separator 224. The liquid condensate, containing methanol, is withdrawn, through line 225 and pressure-reducing valve 226, as a second product mixture E1, from the synthesis loop, and is fed through the collecting line 245 to the intermediate pressure-reducing vessel 253. The gaseous components from the separator 224 are drawn through line 227, are combined with the warm product mixture component from line 228, and are led to the synthesis stage 203 through line 229 as flow C2.

The flow ratio of line 228 and line 227 is governed by the temperature control at the inlet of synthesis stage 203. The product mixture flow D2 is withdrawn through line 230 from synthesis stage 3 and is fed to the gas-gas heat exchanger 231. Here, it cools down and heats the mixture of make-up gas and recycle gas, which is fed through line 244 to the first synthesis stage. Some of the product gas D2 is used, through line 255, also for heat recovery in the heat exchanger 254. The heat is transferred to the completely desalinated water, line 256, and the cooled product gas is fed through line 257 to the product gas at the outlet from the heat exchanger 231. The mixture is fed, through line 233, to the water cooler 234 and is cooled down to 40° C., the water and methanol vapors condense and are fed through line 235 to the separator 236.

Here, the liquid methanol containing condensate separates from the gaseous components. The condensate, flow E2, is fed through line 237 and pressure-reducing valve 238 in the collecting line 245 and the intermediate pressure-reducing vessel 253. The gaseous components are withdrawn through line 239 from the separator 236 and are divided into two partial flows. The recycle gas is drawn through line 240 by the rotary compressor 232, and the purge gas is depressurized through line 241 from the synthesis loop in order to avoid accumulation of inert gases. The raw methanol is led, from the pressure-reducing vessel 253, through line 248, the pressure-reducing valve 249 and line 250 to a conventional distillation process, which is not shown. The preheated boiler feed water (208 and 220) as well as the preheated and completely desalinated water (208', 220' and 256) are fed to a steam generator outside the synthesis loop.

Figure 3:
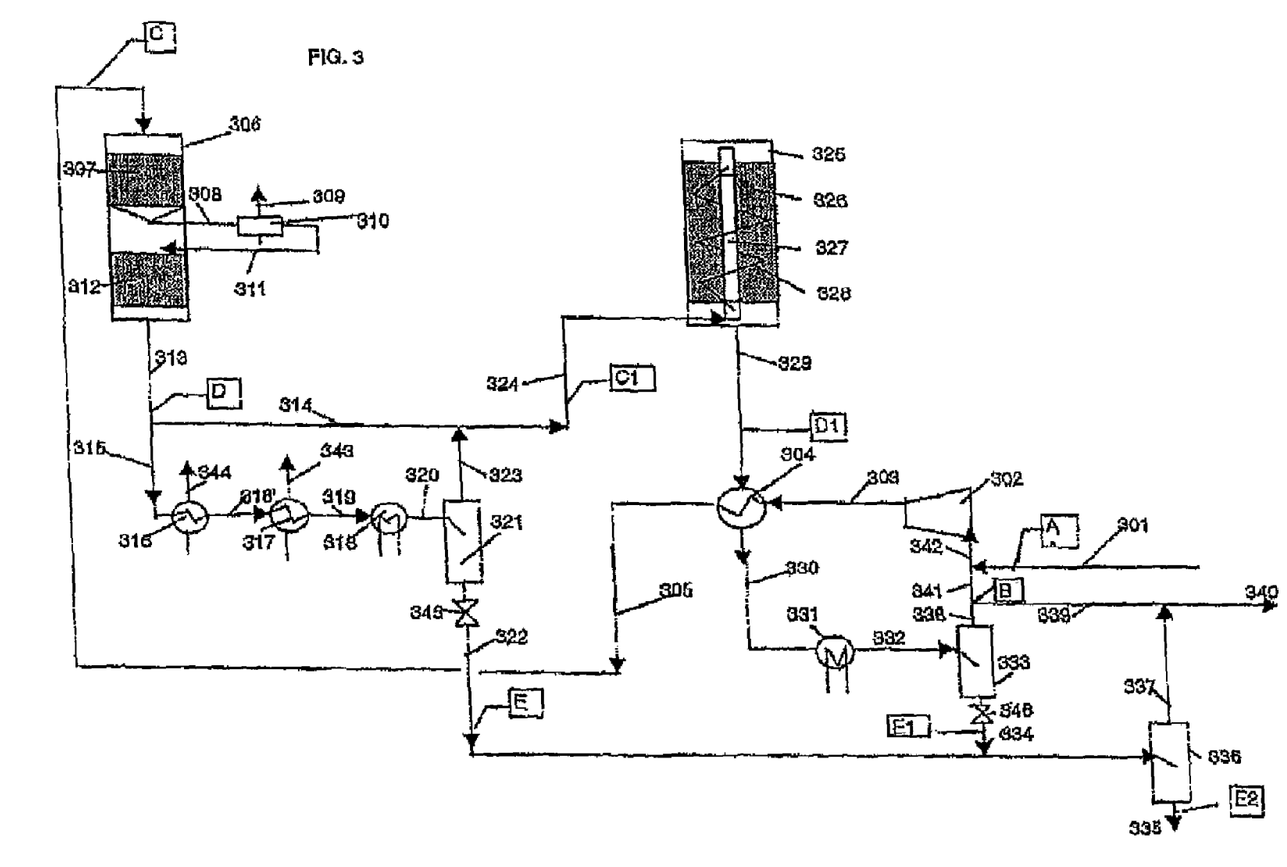
FIG. 3 shows a flow chart of the method with two synthesis stages, FIG. 3-A shows another alternative of the method with two synthesis stages and FIG. 3-B shows another alternative of the method with two synthesis stages.

According to FIG. 3, a mixture of make-up and recycle synthesis gas is fed through line 305, as flow C, into the first synthesis reactor 306. This first synthesis reactor is a conventional adiabatically operated shaft reactor, containing the copper catalyst, with two beds 307 and 312, with indirect intermediate cooling. The coolant is boiler feed water 309, which is fed through the heat exchanger 310, a steam generator, into the gas generating apparatus. The product mixture from the catalyst bed 307 is withdrawn through line 308 and fed through the heat exchanger 310, transferring some of its heat to the boiler feed water, and cools down to the inlet temperature of the catalyst bed 312.

Flow D, the product mixture from the first synthesis reactor 306, is withdrawn through line 313 and is divided into two partial flows. One warm partial flow of the product mixture D is fed through line 314. The other partial flow of product mixture D is fed through line 315 through the heat exchangers 316 and 317, and finally it is cooled down in the water cooler 318 to 40° C. and fed through line 320 into the separating vessel 321. Most of the heat of the product mixture is recovered in the heat exchanger 316 through boiler feed water 344 and in the heat exchanger 317 through the completely desalinated water 343.

The condensed methanol-water mixture is separated, in the separating vessel 321, from the gaseous components, and the first raw methanol flow E is withdrawn from the separating vessel 321 through line 322 and the pressure-reducing valve 345. The gaseous components flow through line 323 out from the separating vessel 321 and are admixed to the warm partial flow of product gas D from line 314, forming flow C1 in line 324, which reaches the inlet temperature in the cooling tubes 328 of the second synthesis reactor. The cooling tubes extend spirally through the synthesis catalyst 326 of the second synthesis reactor, in an upwards direction. The synthesis gas absorbs some of the reaction heat and is therefore preheated to the inlet temperature of the catalyst, and then flows downwards through the synthesis catalyst.

The product mixture D1 is withdrawn through line, 329 from the synthesis reactor and is fed through the heat exchanger 304, in which it is cooled, at the same time preheating the mixture of the make up and recycle synthesis gas, fed by the rotary compressor 302, to the inlet temperature in the first synthesis reactor, as flow C. The product mixture D1 then flows further through line 330 in the water cooler 331, where it is cooled down to 40° C. and reaches, through line 332, the separating vessel 333, in which gases are separated from liquids. The gaseous components are withdrawn through line 338, wherein part of these components are removed from the process through line 339. The synthesis gases to be recycled from line 341, together with the make-up gas from line 301 are drawn by the rotary compressor 302 and fed in an already described manner to the first synthesis reactor 306, as flow C.

Methanol rich condensate is withdrawn from the separating vessel 333, as flow E1, through the pressure-reducing valve 346 and line 334, and, together with flow E from the separating vessel 321, the entire raw methanol is led into the pressure-reducing vessel 336. Residual gas is drawn through line 337 and raw methanol is withdrawn through line 335, and then purified in a conventional way in a plant not shown in the drawings.

FIG. 3-A shows a flow chart of the method according to the invention, in which both synthesis reactors 306 and 325 are cooled by indirect heat exchange with synthesis gas, which flows through spiral tubes, which cross the catalyst. In addition to the embodiments of FIG. 3, a further heat exchanger 310 is provided, for further heat recovery from the second product gas, i.e. flow D1. Through line 330, the product mixture D1 is fed from heat exchanger 304 to heat exchanger 310, and through line 311 further to the water end cooler 331. In the heat exchanger 310, some of the heat is absorbed from the fully desalinated water 312 and is used to generate steam in synthesis gas production, which is not shown here. The remaining reference numerals and flow numbers have the already explained meaning.

FIG. 3-B shows an embodiment of the method according to the invention, in which the first synthesis reactor 306 is an isothermal synthesis reactor. The catalyst charge 307 is crossed by coiled cooling tubes 348, in which as a refrigerant, water boiling at an elevated pressure flows in a natural or forced circulation 311. A mixture of vapor and boiling water is withdrawn through line 346 and fed to a vapor drum (pot shown). In order to pre-heat the mixture of make-up gas and recycle gas, i.e. flow C, in line 305, up to the inlet temperature in the first synthesis reactor 306, the gas mixture is fed also through the heat exchanger 316, by means of lines 349 and 350. The remaining reference numerals and flow numbers have the same meaning as in FIGS. 3 and 3-A.

Hereunder the operation of the methanol plant according to the invention is explained, wherein examples 2, 3 and 4 of table I are based on the arrangements of FIG. 2 and FIG. 3, 3-A respectively. On the other hand, example 1 is a comparative example according to the state of the art and corresponds to FIG. 2, although without raw methanol separation after the synthesis stages 201 and 202, without the heat exchangers 251' and 252', without the water coolers 210 and 222 and without the separators 212 and 224. The product gases 206 and 218 are no longer divided into two partial flows; instead they are fed, after heat transfer in heat exchangers 251 and 252, directly to the following synthesis stage. Data of the examples are obtained through calculation. For a clearer overview and for comparative purposes, data are shown in tabular form.

TABLE 1

| | Ex. 1 | Ex. 2 | Ex. 3 | Ex. 4 |
|---|---|---|---|---|
| Flow (A) | | | | |
| Nm³/h | 600000 | 750000 | 600000 | 600000 |
| H$_2$ (Mol-%) | 71.5 | 71.5 | 71.50 | 71.50 |
| CO (Mol-%) | 16.5 | 16.5 | 16.50 | 16.50 |
| CO$_2$ (Mol-%) | 8.2 | 8.2 | 8.20 | 8.20 |
| Inerts (Mol-%) | 3.8 | 3.8 | 3.80 | 3.80 |
| Circulation ratio | 1:6 | 1:4.6 | 1:3.5 | 1:2.7 |
| Flow (B) | | | | |
| H$_2$ (Mol-%) | 78.38 | 78.17 | 78.35 | 78.26 |
| CO (Mol-%) | 0.60 | 1.00 | 0.56 | 0.56 |
| CO$_2$ (Mol-%) | 0.61 | 1.00 | 0.85 | 1.46 |
| Flow (c) | | | | |
| H$_2$ (Mol-%) | 77.40 | 76.98 | 76.83 | 76.44 |
| CO (Mol-%) | 2.87 | 3.77 | 4.10 | 4.86 |
| CO$_2$ (Mol-%) | 1.69 | 2.29 | 2.53 | 3.28 |
| Others (Mol-%) | 18.04 | 16.96 | 16.54 | 15.42 |
| Temp. (° C.) | 230.50 | 227.50 | 230.00 | 114.25 |
| Pressure (bar) | 101 | 101 | 101 | 101 |
| Load (Nm³/h/m³·h) | 34000 | 34000 | 17420 | 14300 |
| Flow (D) | | | | |
| CH$_3$OH (Mol-%) | 2.09 | 2.16 | 4.33 | 5.43 |
| H$_2$ (Mol-%) | 75.87 | 75.36 | 73.62 | 72.51 |
| CO (Mol-%) | 1.86 | 2.75 | 1.68 | 1.67 |
| CO$_2$ (Mol-%) | 1.05 | 1.64 | 1.42 | 2.14 |
| Others (Mol-%) | 19.13 | 18.09 | 18.95 | 18.25 |
| Temp. (° C.) | 276.3 | 275.3 | 283.8 | 240.3 |
| Flow (C1) | | | | |
| CH$_3$OH (Mol-%) | 2.09 | 1.83 | 2.91 | 3.27 |
| H$_2$ (Mol-%) | 75.87 | 75.73 | 75.1 | 74.68 |
| CO (Mol-%) | 1.86 | 2.76 | 1.71 | 1.72 |
| CO$_2$ (Mol-%) | 1.05 | 1.65 | 1.45 | 2.20 |
| Others (Mol-%) | 19.30 | 19.03 | 18.83 | 18.13 |
| Temp. (° C.) | 240.5 | 235 | 202 | 159.7 |
| Flow (E) | | | | |
| CH$_3$OH (To/24 h) | | 473.96 | 1261.6 | 1550.9 |
| Flow (D1) | | | | |
| CH$_3$OH (Mol-%) | 3.40 | 3.49 | 4.92 | 5.65 |
| H$_2$ (Mol-%) | 74.95 | 74.55 | 73.5 | 72.6 |
| CO (Mol-%) | 0.95 | 1.65 | 0.53 | 0.52 |
| CO$_2$ (Mol-%) | 0.77 | 1.3 | 0.85 | 1.35 |
| Others (Mol-%) | 19.92 | 19.01 | 20.2 | 19.88 |
| Temp. (° C.) | 274.3 | 277.3 | 216 | 216 |
| Flow (E1) | | | | |
| CH$_3$OH (To/24 h) | | 640.22 | 3752 | 3440 |
| Flow (C2) | | | | |
| CH$_3$OH (Mol-%) | 3.40 | 3.03 | — | — |
| H$_2$ (Mol-%) | 74.95 | 75.02 | — | — |
| CO (Mol-%) | 0.95 | 1.66 | — | — |
| CO$_2$ (Mol-%) | 0.77 | 1.31 | — | — |
| Others (Mol-%) | 19.92 | 18.98 | — | — |
| Temp. (° C.) | 253 | 245 | — | — |
| Flow (D2) | | | | |
| CH$_3$OH (Mol-%) | 4.04 | 4.23 | — | — |
| H$_2$ (Mol-%) | 74.46 | 74.07 | — | — |
| CO (Mol-%) | 0.57 | 0.95 | — | — |
| CO$_2$ (Mol-%) | 0.58 | 0.95 | — | — |
| Others (Mol-%) | 20.35 | 19.80 | — | — |
| Temp. (° C.) | 268.3 | 273.5 | — | — |
| Flow (E2) | | | | |
| CH$_3$OH (To/24 h) | 5024 | 5125.5 | 5013.6 | 4990.9 |
| Flow (E3) | | | | |
| CH$_3$OH (To/24 h) | 5024 | 6240 | — | |

The total catalyst quantity in examples 1 and 2 are the same. In example 3 the total catalyst quantity is divided according to the ratio 1:1.2 among synthesis reactors 6 and 25. In example 4 the total catalyst quantity is divided according to the ratio 1:1.25 among the two synthesis reactors. In examples 3 and 4, the catalyst quantity is 8% less than in example 1.

Further examples are given in table 2. In table 2, example 5 corresponds to the state of the art and example 6 corresponds to the method of the invention according to FIG. 3-B. For comparative purposes a make-up gas composition with a CO:CO2 ratio equal to approximately 1:1 is used. In example 5, the product mixture from the first synthesis reactor 6, i.e. flow D, from line 313, FIG. 3-B, is not divided into two partial flows and is not cooled down, but instead it is fed directly as flow C1 to the upper part of the second synthesis reactor 325 and flows downwards through the catalyst bed 326. The mixture of recycle and make-up gas, i.e. flow C, from line 305, FIG. 3B, is fed directly to the lower inlet of the spiral tubes 328, FIG. 3B, then flows upwards through the tubes and leaves the second synthesis reactor on the upper side and is fed further on to the inlet in the catalyst bed 307 of the first synthesis reactor 306. The entire raw methanol quantity is withdrawn from the second product mixture, i.e. flow D1, FIG. 3B, after cooling down, from the separator 333.

TABLE 2

|  | Example 5 | Example 6 |
|---|---|---|
| Flow (A) | | |
| Nm³/h | 600000 | 600000 |
| H₂ (Mol-%) | 71.138 | 71.138 |
| CO (Mol-%) | 12.819 | 12.819 |
| CO₂ (Mol-%) | 12.621 | 12.621 |
| Inerts (Mol-%) | 3.422 | 3.422 |
| Circulation ratio | 1:2.7 | 1:2.7 |
| Flow (B) | | |
| H₂ (Mol-%) | 71.82 | 71.32 |
| CO (Mol-%) | 1.99 | 1.53 |
| CO₂ (Mol-%) | 8.38 | 4.86 |
| Flow (C) | | |
| H₂ (Mol-%) | 71.64 | 71.27 |
| CO (Mol-%) | 4.92 | 4.58 |
| CO₂ (Mol-%) | 9.52 | 6.96 |
| Others (Mol-%) | 13.92 | 17.19 |
| Temp. (° C.) | 230 | 230 |
| Pressure (bar) | 82.6 | 82.6 |
| Load (Nm³/h/m³ · h) | 18500 | 17100 |
| Flow (D) | | |
| CH₃OH (Mol-%) | 5.45 | 4.93 |
| H₂ (Mol-%) | 65.72 | 66.26 |
| CO (Mol-%) | 3.19 | 2.64 |
| CO₂ (Mol-%) | 7.55 | 5.30 |
| Others (Mol-%) | 18.11 | 20.87 |
| Temp. (° C.) | 266.7 | 264 |
| Flow (C1) | | |
| CH₃OH (Mol-%) | 5.45 | 2.76 |
| H₂ (Mol-%) | 65.72 | 65.62 |
| CO (Mol-%) | 3.19 | 2.74 |
| CO₂ (Mol-%) | 7.55 | 5.49 |
| Others (Mol-%) | 18.11 | 20.39 |
| Temp. (° C.) | 266.7 | 163.55 |
| Flow (E) | | |
| CH₃OH (To/24 h) | | 1576.05 |
| Flow (D1) | | |
| CH₃OH (Mol-%) | 7.56 | 5.72 |
| H₂ (Mol-%) | 64.04 | 65.53 |
| CO (Mol-%) | 1.78 | 1.41 |
| CO₂ (Mol-%) | 7.47 | 4.47 |
| Others (Mol-%) | 19.15 | 22.87 |
| Temp. (° C.) | 218 | 226 |
| Flow (E1) | | |
| CH₃OH (To/24 h) | 4841 | 3461.4 |
| Flow (E2) | | |
| CH₃OH (To/24 h) | | 5037.4 |

In examples 5 and 6, the catalyst quantities are the same. In example 6 the CO2 yield is 6.3% higher than in example 5, which represents an advantage of the method according to the invention.

Figure 4:
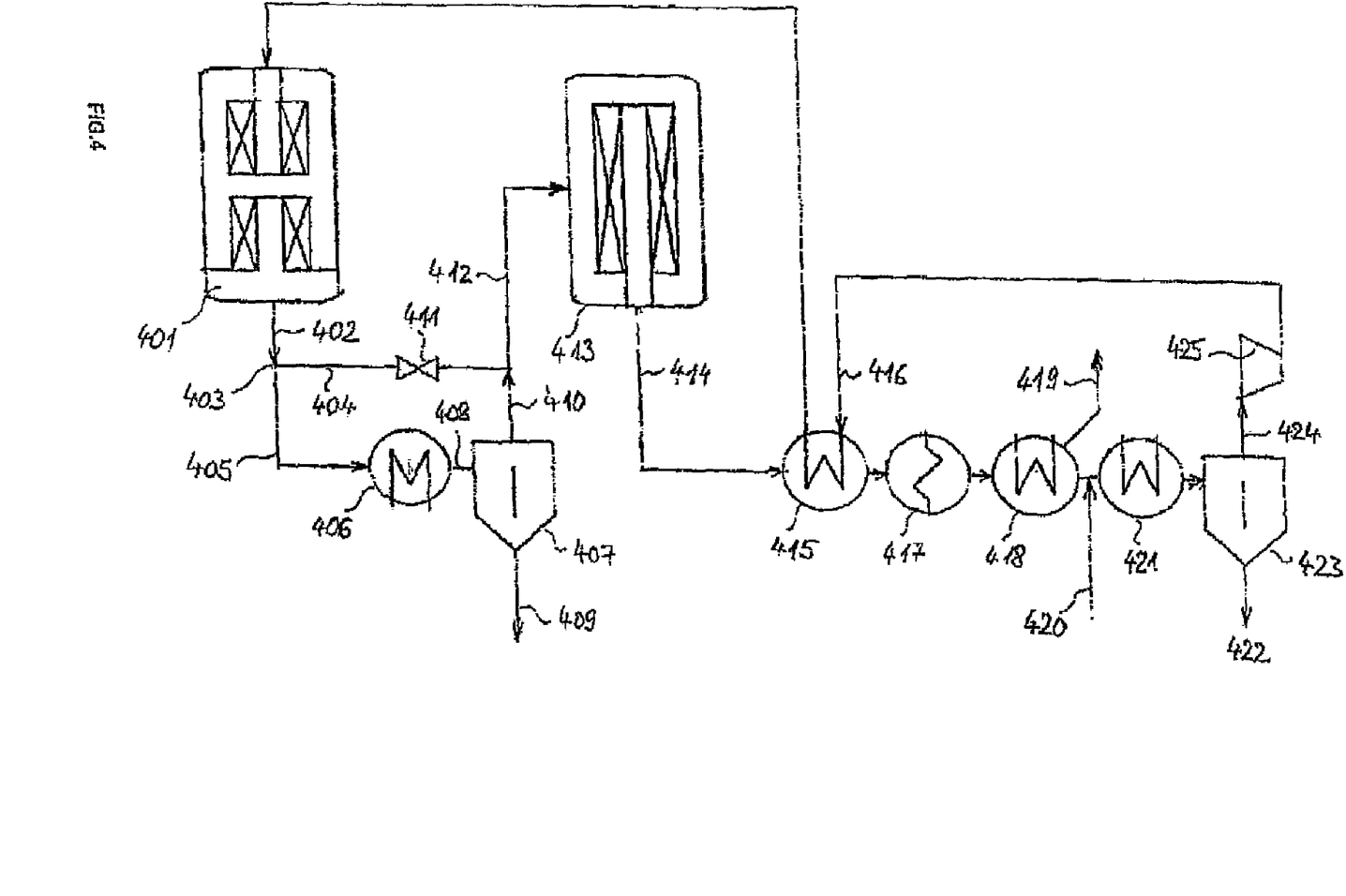
FIG. 4 shows a diagram of the method without partial flow re-heating.

The following drawings and examples of calculations refer to ammonia production. FIG. 4 shows the method of the invention according to the independent claim, in a conventional ammonia plant, in which two ammonia reactors are provided inside a synthesis loop. The hot product gas 402 leaving the first synthesis reactor 401 is divided at the separation point 403 into a bypass flow 404 and a partial flow 405, which is cooled in a cascading arrangement of heat exchangers, which are here symbolically represented by the heat exchanger 406, in such a way that most of the ammonia contained in the partial flow 405 is condensed out, and is then extracted in the separator 407 from the cooled partial flow 406, as liquid ammonia 409.

The reduced partial flow 410 is combined with the hot bypass flow 404, under the control of the control valve 411, and forms the working flow 412 fox the second synthesis reactor 413, where further conversion into ammonia is carried out. The hot product gas 414 leaving the second synthesis reactor 413 is cooled in the gas-gas heat exchanger 415 by the synthesis gas 416 of the first synthesis reactor 401 to be warmed, then it is conventionally fed to a steam generator 417, then cooled down to ambient temperature, a purge gas 419 being withdrawn, make-up gas 420 is admixed, the product gas is deep cooled in the chiller 421 and liquid ammonia 422 is separated in the ammonia separator 423. The cold synthesis gas 424 is fed by the circulation compressor 425 to the gas-gas heat exchanger 415, where it is reheated before being used in the first synthesis reactor 401.

Figure 5:
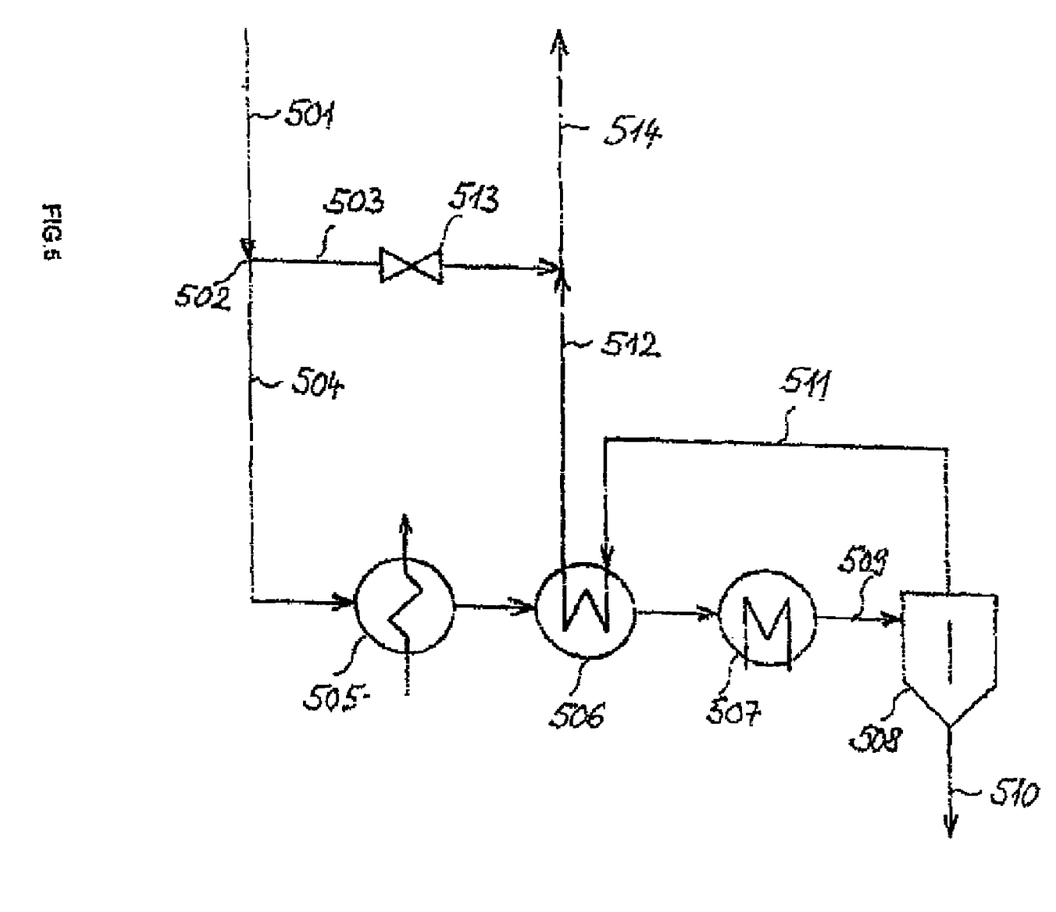
FIG. 5 shows a diagram of the method with partial flow re-heating and steam generation.

FIG. 5 shows the method of the invention according to claim 3, used in a conventional ammonia plant according to FIG. 41 wherein the synthesis reactors as well as the ammonia extraction, positioned before the circulation compression, need not be shown, since they are identical to FIG. 4. The hot product gas 501 (corresponds to 402) leaving the first synthesis reactor is divided at the separation point 502 (corresponds to 403) into a bypass flow 503 (corresponds to 404) and a partial flow 504 (corresponds to 405). This partial flow 504 is initially fed to a steam generator 505 and then to a gas-gas heat exchanger 506, which provides most of the cooling. In the post-cooling system 507 (corresponds to 406), the partial flow 504 is cooled so that most of the ammonia contained condenses out, and is extracted in the separator 508 (corresponds to 407) from the cooled partial flow 509 (corresponds to 408) as liquid ammonia 510 (corresponds to 409).

The reduced partial flow 511 is reheated in the gas-gas heat exchanger 506 and only successively combined, as a mixing flow 512, with the hot bypass flow 503, controlled by the control valve 513, and forms the synthesis gas flow 514 for the following synthesis reactor (not shown). By selecting the mixing ratio of flows 503 and 504 as well as by choosing the cooling system 507, it is possible to set arbitrarily low ammonia concentrations in flow 514. The less the ammonia concentrations chosen in flow 514, the higher is the expected temperature increase in the following reactor, and the lower the required reactor inlet temperature.

Therefore, the person skilled in the art has a degree of freedom in case of retrofittings, in which reactors already present have to be used. Low inlet temperatures are preferred in reactors which are provided with two catalyst beds and one internal heat exchange. Higher inlet temperatures are used in, reactors with a single catalyst bed. If a low inlet temperature is chosen, the mixing ratio of flows 503-504 is as low as possible and can also reach zero, and the percentage of ammonia which has to be separated from flow 509 is as high as possible. In this, case, it is possible to generate a lot of high pressure steam in the steam generator 505, because of a very high energy excess.

If a higher inlet temperature is chosen, the mixing ratio of flows 503-504 is relatively high and the ammonia percentage, which has to be separated from flow 509, is lower. In this case, in the steam generator 505 only a small amount of high pressure steam can be generated, because of the absence of a high energy surplus. On the other hand, requirements in reactors, heat exchangers and, for ammonia condensation are lower. In designing retrofittings with a plurality of reactors, the skilled in the art may also apply different concepts for the individual reactors according to the invention, wherein it is possible to use every known reactor type.

The advantages of the invention are also evident in the following 4 calculation examples 7-10, which are summarized in table 3. Example 7 is the comparative example according to the state of the art and corresponds to the arrangement of FIG. 4, in which the partial flow 405 represents the limit with zero flow rate. Example 8 shows the arrangement of FIG. 4, by applying the invention according to the independent claim. Example 9 shows another embodiment according to claim 3, as shown in FIG. 5, where flow 514 is successively fed, at a higher reactor inlet temperature, into a reactor with one catalyst bed. Example 10 also, shows another embodiment according to claim 3, as shown in FIG. 5, where flow 514 is fed at lower reactor inlet temperature into a reactor with two catalyst beds and internal heat exchange.

TABLE 3

| Example 7 | | | | | | |
|---|---|---|---|---|---|---|
| | | 420 | 402 | 412 | 419 | 422 |
| $CH_4$ | Mol-% | 1.17 | 9.27 | 9.27 | 13.66 | |
| Ar | Mol-% | 0.36 | 3.11 | 3.11 | 4.20 | |
| $H_2$ | Mol-% | 73.54 | 50.94 | 50.94 | 55.81 | |
| $N_2$ | Mol-% | 24.93 | 20.49 | 20.49 | 22.32 | |
| $NH_3$ | Mol-% | | 16.19 | 16.19 | 4.00 | 100 |
| Sum | | 100.00 | 100.00 | 100.00 | 100.00 | |
| Flow Rate | kmol/h | 10856 | 34284 | 34284 | 930 | 4957 |
| Pressure | bar | 198 | | | | |
| Temp. | ° C. | 46 | 480 | 412 | 4 | 0 |

| Example 8 | | | | | | |
|---|---|---|---|---|---|---|
| | | 420 | 402 | 412 | 419 | 422 |
| $CH_4$ | Mol-% | 1.17 | 9.27 | 9.47 | 13.66 | |
| Ar | Mol-% | 0.36 | 3.11 | 3.18 | 4.20 | |
| $H_2$ | Mol-% | 73.54 | 50.94 | 52.09 | 55.81 | |
| $N_2$ | Mol-% | 24.93 | 20.49 | 20.95 | 22.32 | |
| $NH_3$ | Mol-% | | 16.19 | 14.31 | 4.00 | 100 |
| Sum | | 100.00 | 100.00 | 100.00 | 100.00 | |
| Flow Rate | kmol/h | 11247 | 34284 | 33519 | 963 | 4370 |
| Pressure | bar | 198 | | | | |
| Temp. | ° C. | 46 | 480 | 410 | 4 | 0 |

| | | 405 | 404 | 409 | 410 |
|---|---|---|---|---|---|
| $CH_4$ | Mol-% | 9.27 | 9.27 | | 10.58 |
| Ar | Mol-% | 3.11 | 3.11 | | 3.55 |
| $H_2$ | Mol-% | 50.94 | 50.94 | | 58.36 |
| $N_2$ | Mol-% | 20.49 | 20.49 | | 23.47 |
| $NH_3$ | Mol-% | 16.19 | 16.19 | 100 | 4.04 |
| Sum | | 100.00 | 100.00 | 100.00 | 100.00 |
| Flow Rate | kmol/h | 5969 | 28315 | 765 | 5204 |
| Pressure | bar | | | | |
| Temp. | ° C. | 480 | 480 | 0 | 0 |

| Example 9 | | | | | | |
|---|---|---|---|---|---|---|
| | | 420 | 501 | 514 | 419 | 422 |
| $CH_4$ | Mol-% | 1.17 | 9.27 | 9.88 | 13.66 | |
| Ar | Mol-% | 0.36 | 3.11 | 3.32 | 4.20 | |
| $H_2$ | Mol-% | 73.54 | 50.94 | 54.39 | 55.81 | |

TABLE 3-continued

| $N_2$ | Mol-% | 24.93 | 20.49 | 21.88 | 22.32 | |
|---|---|---|---|---|---|---|
| $NH_3$ | Mol-% | | 16.19 | 10.53 | 4.00 | 100 |
| Sum | | 100.00 | 100.00 | 100.00 | 100.00 | |
| Flow Rate | kmol/h | 12267 | 34284 | 32089 | 1050 | 3406 |
| Pressure | bar | 198 | | | | |
| Temp. | ° C. | 46 | 480 | 410 | 4 | 0 |

| | | 504 | 503 | 510 | 511 |
|---|---|---|---|---|---|
| $CH_4$ | Mol-% | 9.27 | 9.27 | | 10.58 |
| Ar | Mol-% | 3.11 | 3.11 | | 3.55 |
| $H_2$ | Mol-% | 50.94 | 50.94 | | 58.36 |
| $N_2$ | Mol-% | 20.49 | 20.49 | | 23.47 |
| $NH_3$ | Mol-% | 16.19 | 16.19 | 100 | 4.04 |
| Sum | | 100.00 | 100.00 | 100.00 | 100.00 |
| Flow Rate | kmol/h | 17142 | 17142 | 2195 | 14947 |
| Pressure | bar | | | | |
| Temp. | ° C. | 480 | 480 | 0 | 0 |

| Example 10 | | | | | | |
|---|---|---|---|---|---|---|
| | | 420 | 501 | 514 | 419 | 422 |
| $CH_4$ | Mol-% | 1.17 | 9.27 | 10.58 | 13.66 | |
| Ar | Mol-% | 0.36 | 3.11 | 3.55 | 4.20 | |
| $H_2$ | Mol-% | 73.54 | 50.94 | 58.36 | 55.81 | |
| $N_2$ | Mol-% | 24.93 | 20.49 | 23.47 | 22.32 | |
| $NH_3$ | Mol-% | | 16.19 | 4.04 | 4.00 | 100 |
| Sum | | 100.00 | 100.00 | 100.00 | 100.00 | |
| Flow Rate | kmol/h | 15741 | 34284 | 29896 | 1348 | 2799 |
| Pressure | bar | 198 | | | | |
| Temp. | ° C. | 46 | 480 | 305 | 4 | 0 |

| | | 504 | 503 | 510 | 511 |
|---|---|---|---|---|---|
| $CH_4$ | Mol-% | 9.27 | 9.27 | | 10.58 |
| Ar | Mol-% | 3.11 | 3.11 | | 3.55 |
| $H_2$ | Mol-% | 50.94 | 50.94 | | 58.36 |
| $N_2$ | Mol-% | 20.49 | 20.49 | | 23.47 |
| $NH_3$ | Mol-% | 16.19 | 16.19 | 100 | 4.04 |
| Sum | | 100.00 | 100.00 | 100.00 | 100.00 |
| Flow Rate | kmol/h | 34284 | 0 | 4388 | 29896 |
| Pressure | bar | | | | |
| Temp. | ° C. | 480 | 480 | 0 | 0 |

As is evident from the examples in table 3, the following ammonia quantities are produced:

Example 7

Comparative Case 4957 kmol/h=100%

Example 8

765 kmol/h+4370 kmol/h=5135 kmol/h=103.6%

Example 9

2195 kmol/h+3406 kmol/h=5601 kmol/h=113.0%

Example 10

2799 kmol/h+4388 kmol/h=7187 kmol/h=145.0%.

Even with a loop formed by 2-reactors it is possible to obtain a subsequent capacity increase of almost 50%.

Figure 6:
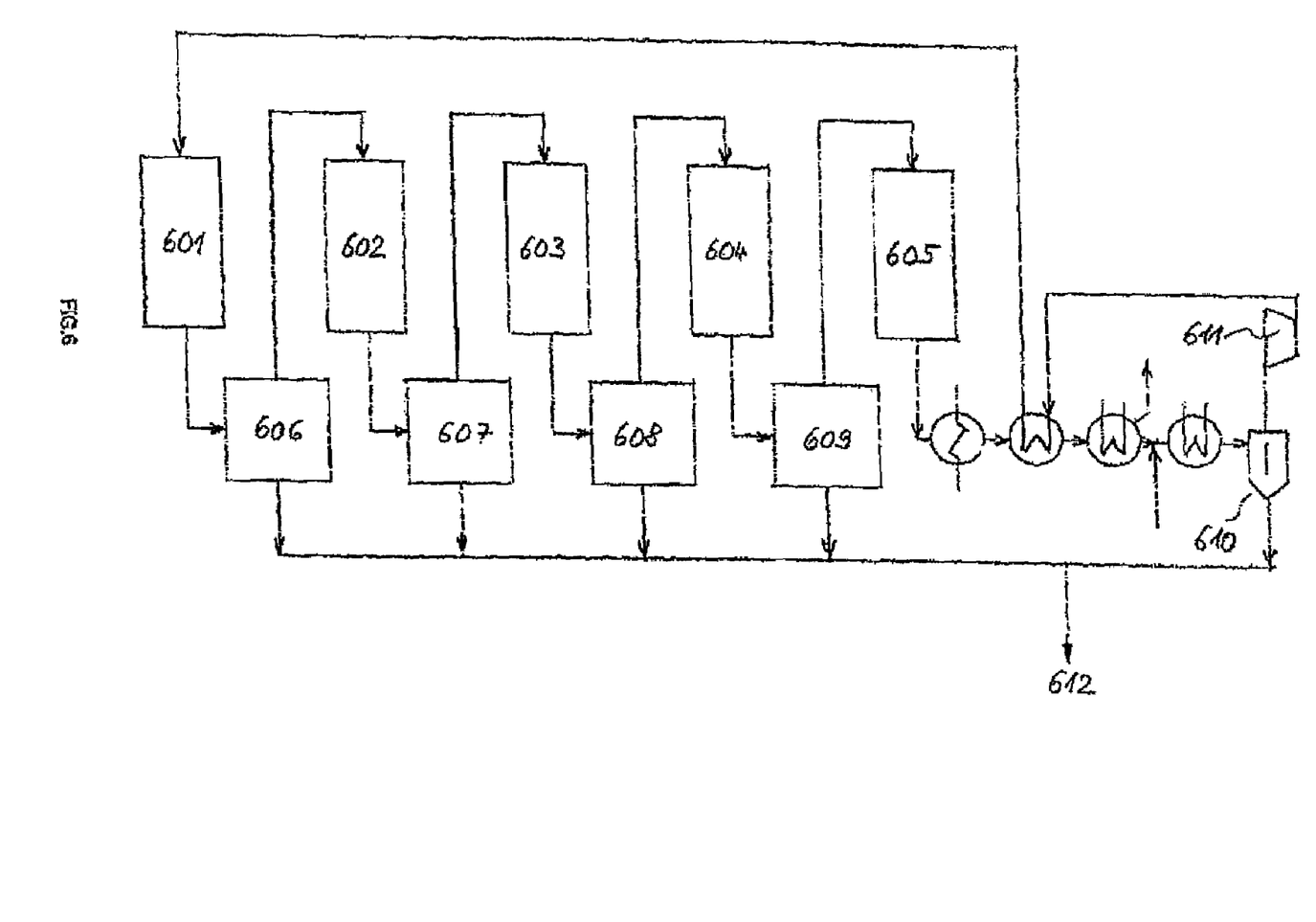
FIG. 6 shows a diagram of the method with 5 reactors.

FIG. 6 shows how it is possible to obtain, by following examples 9 and 10, a capacity increase which is higher than a factor 2. In this case, the five ammonia reactors 601, 602, 603, 604 and 605 are connected in series, although there is no problem to continue using two reactors already present. The reactors can be exactly identical or different from one another, depending on the different situations. Ammonia 612 is obtained from the partial condensation systems 606, 607, 608 and 609, which all correspond to the loop shown in FIG. 5, then it is extracted downstream of the last reactor from the separator 610 where, because of the circulation gas compressor 611, no bypass can be provided after the last reactor.

The invention claimed is:

1. A method for carrying out heterogeneous catalytic exothermic gas phase reactions at high temperature and pressure, the method comprising the steps of:
    feeding the synthesis gas comprised of a mixture of make-up gas and/or of recycle gas through at least two synthesis stages that are connected in-series to form a synthesis system
        separating the product gases from the synthesis stages, with the exception of the last stage, into at least two partial flows;
        cooling one partial flow until the product is condensated out, and separating the condensate containing the product from the gaseous constituents; and
        subsequently, combining the gaseous constituents with the warm portion of the product gas in order to reach the inlet temperature of the following synthesis stage.

2. Method according to claim 1, wherein the partial flow, from which the product has been condensated out and removed, is heated before its remixing with the warm portion of the product gas, wherein the temperature after heating is lower than the temperature of the warm portion of the product gas.

3. Method according to claim 2, wherein the heat used for heating the partial flow, from which the product has been condensated out, is at least partially recovered from the cooling of this partial flow.

4. Method according to claim 1, wherein from the portion of the product gas to be cooled, most of the heat is recovered by indirect heat exchange with boiler feed water and/or totally desalinated water.

5. Method according to claim 1, wherein the synthesis gas led into the first synthesis reactor is composed of 16 to 40 mol-% of make-up synthesis gas.

6. Method according to claim 1, wherein the last reactor of a synthesis system is cooled by indirect heat exchange with synthesis gas.

7. Method according to claim 1, wherein methanol is obtained from a synthesis gas containing hydrogen, carbon monoxide and carbon dioxide, by conversion on granular, copper containing catalysts, at pressures between 20 and 120 bar and temperatures between 200 and 350° C. and in that, between the first and last synthesis stage, 15 to 50% of the total methanol production is present in the separated methanol containing condensate.

8. Method according to claim 7, wherein the first synthesis reactor is an adiabatic multiple bed reactor.

9. Method according to claim 7, wherein the first reactor is a tube reactor with synthesis gas cooling.

10. Method according to claim 7, wherein the first synthesis reactor is an isothermal reactor.

11. Method according to claim 10, wherein the catalyst is crossed by tubes, in which water, boiling at elevated pressure, flows.

12. Method according to claim 2, wherein at least 3 ammonia reactors are connected in series.

13. Method according to claim 1, wherein downstream of each ammonia reactor a cooling vessel is arranged, which converts part of the reaction heat into working steam.

14. Method according to claim 2, wherein heating of the partial flow, from which ammonia has condensated out, is supported by heat transfer from a successive reactor.

* * * * *